United States Patent [19]

Skuballa et al.

[11] Patent Number: 4,886,788
[45] Date of Patent: Dec. 12, 1989

[54] CYCLODEXTRIN CLATHRATES OF CARBACYCLIN DERIVATIVES AND THEIR USE AS MEDICINAL AGENTS

[75] Inventors: Werner Skuballa; Helmut Vorbrueggen; Helmut Dahl; Claus-Steffen Stuerzebecher; Karl-Heinz Thierauch, all of Berlin, Fed. Rep. of Germany

[73] Assignee: Schering Aktiengesellschaft, Berlin and Bergkamen, Fed. Rep. of Germany

[21] Appl. No.: 23,506

[22] Filed: Mar. 9, 1987

[30] Foreign Application Priority Data

Mar. 7, 1986 [DE] Fed. Rep. of Germany ....... 3608088

[51] Int. Cl.$^4$ .................... A61K 31/557; C08B 37/16; C07C 177/00
[52] U.S. Cl. ......................................... 514/58; 536/46; 536/103; 560/119; 514/691; 514/729
[58] Field of Search .................. 514/691, 729, 58; 560/119; 536/46, 103

[56] References Cited

U.S. PATENT DOCUMENTS

| | | | |
|---|---|---|---|
| 3,816,393 | 6/1974 | Hayashi et al. ........................ | 560/2 |
| 4,444,788 | 4/1984 | Skuballa et al. ...................... | 514/255 |
| 4,454,339 | 6/1984 | Skuballa et al. ...................... | 514/255 |
| 4,680,307 | 7/1987 | Muraoka et al. ..................... | 514/622 |
| 4,699,921 | 10/1987 | Shibasaki et al. ................... | 514/530 |
| 4,721,729 | 1/1988 | Skuballa et al. ..................... | 514/691 |
| 4,757,087 | 7/1988 | Kojima et al. ........................ | 514/510 |

FOREIGN PATENT DOCUMENTS

| | | |
|---|---|---|
| 6451174 | 7/1975 | Australia . |
| 2840142 | 4/1979 | Fed. Rep. of Germany . |
| 56-150039 | 11/1981 | Japan . |

OTHER PUBLICATIONS

Kirk-Othmer, *Concise Encyclopedia of Chemical Technology*, 1985, pp. 282–283, J. Wiley & Sons, New York.
March, J., *Advanced Organic Chemistry*, "Reactions, Mechanisms, and Structure", pp. 79–80, J. Wiley & Sons, New York.
Abstract of JP application 053056 filed Apr. 20, 1980.

*Primary Examiner*—Ronald W. Griffin
*Attorney, Agent, or Firm*—Millen, White & Zelano

[57] ABSTRACT

Cyclodextrin clathrates of carbacyclin analogs of general Formula I

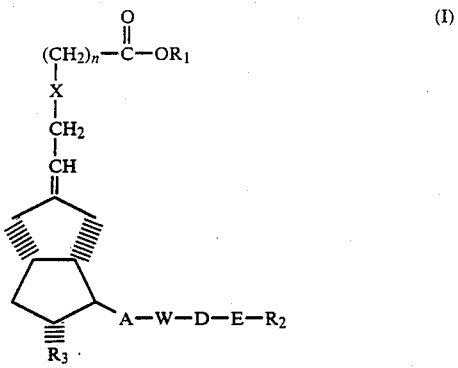

wherein
$R_1$ is hydrogen, alkyl or alkenyl of up to 10 carbon atoms,
A is a —$CH_2CH_2$—, trans—CH=CH—, or —C≡C— group,
W is a free or functionally modified hydroxymethylene group or a free or functionally modified

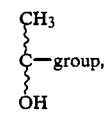

wherein
the OH-group can be in the $\alpha$- or $\beta$-position,
D is

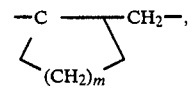

alkylene, or unsaturated alkylene each of which can optionally be substituted by fluorine atoms,
m is 1, 2 or 3,
E is a direct bond, a —C≡C— group, or —$CR_4$=C-$R_5$— group, wherein $R_4$ is hydrogen or an alkyl group of 1–5 carbon atoms, and $R_5$ is hydrogen or an alkyl group of 1–5 carbon atoms, and $R_5$ is hydrogen, halogen, or an alkyl group of 1–5 carbon atoms,
$R_2$ is alkyl or alkenyl of up to 10 carbon atoms, cycloalkyl of 3–10 carbon atoms or an optionally substituted aryl group of 6–10 carbon atoms, or a heterocyclic group, and
$R_3$ is a free or functionally modified hydroxy group,
n is 1, 2, 3, 4 or 5, and
X is —$CH_2$— or oxygen
as valuable crystalline pharmaceuticals.

22 Claims, No Drawings

CYCLODEXTRIN CLATHRATES OF CARBACYCLIN DERIVATIVES AND THEIR USE AS MEDICINAL AGENTS

BACKGROUND OF THE INVENTION

The present invention relates to cyclodextrin clathrates of carbacyclin analogs, and agents containing same.

Carbacyclin analogs are pharmacologically and medicinally valuable active agents, the preparation and use of which have been described, for example, in DOS's 2,845,770, 3,306,123, 3,226,550. These compounds exhibit a substantially improved specificity and, above all, a substantially longer period of effectiveness, with a similar spectrum of activity, as compared with the corresponding natural prostacyclin.

The carbacyclin analogs described in the abovementioned laid-open applications frequently are not present in crystalline form whereby limits are imposed on their pharmaceutical usage. Additionally, they also exhibit limited water solubility and dissolution rates.

SUMMARY OF THE INVENTION

It is an object of this invention to provide new compounds having valuable pharmacological properties and which ameliorate the foregoing problem.

Upon further study of the specification and appended claims, further objects and advantages of this invention will become apparent to those skilled in the art.

It has now been found that inclusion compounds of these carbacyclin analogs with cyclodextrins do not show the aforementioned disadvantages or possess them to a lower degree, i.e., their water solubility is improved, their dissolution rate is increased, and the inclusion compounds are present in crystalline form. Furthermore, their stability, for example, with respect to head, light, and oxygen is increased, and their galenic preparation (production of solutions or tablets) is facilitated.

Thus, these objects are achieved, for example, by this invention by providing cyclodextrin clathrates of carbacyclin analogs of Formula I

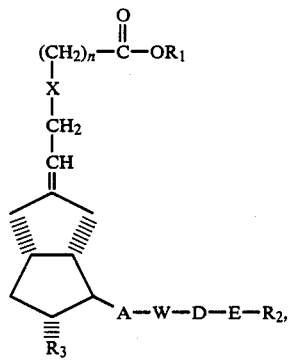

wherein
$R_1$ is a hydrogen atom or a straight-chain or branched alkyl residue of up to 10 carbon atoms,
A is a $-CH_2CH_2-$, trans-$CH=CH-$, or $-C\equiv C-$ group,
W is a free or functionally modified hydroxymethylene group or a free or functionally modified

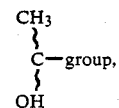

wherein
the OH-group can be in the $\alpha$- or $\beta$-position,
D is the group

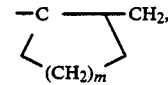

a straight-chain, saturated alkylene group of 1-10 carbon atoms, a branched saturated alkylene group of 2-10 C-atoms, or a straight-chain or branched, unsaturated alkylene group of 2-10 carbon atoms, either of which can optionally be substituted by fluorine atoms,
m is 1, 2 or 3,
E is a direct bond, a $-C\equiv C$-group, or a $-CR_4=C-R_5-$ group wherein $R_4$ is hydrogen or an alkyl group of 1-5 carbon atoms, and $R_5$ is hydrogen, halogen, or an alkyl group of 1-5 carbon atoms,
$R_2$ is an alkyl group of 1-10 carbon atoms, a cycloalkyl group of 3-10 carbon atoms, or an optionally substituted aryl group of 6-10 carbon atoms, or a heterocyclic group, and
$R_3$ is a free or functionally modified hydroxy group,
n is 1, 2, 3, 4 or 5, and
X is a $-CH_2$-group or an oxygen atom.

The compounds of Formula I represent (5E)-as well as (5Z)-isomers.

Suitable alkyl groups $R_1$ and $R_2$ are straight- and branched-chain, saturated and unsaturated alkyl or alkenyl residues, preferably saturated ones of 1-10, in particular 1-7 carbon atoms which can be substituted by optionally substituted aryl (as defined below). Examples include methyl, ethyl, propyl, butyl, isobutyl, tert-butyl, pentyl, hexyl, heptyl, octyl, butenyl, isobutenyl, propenyl, pentenyl, hexenyl, benzyl, and p-chlorobenzyl.

The cycloalkyl groups $R_2$ can contain in the ring 3-10, preferably 3-6 carbon atoms. The rings can be substituted by alkyl groups of 1-4 carbon atoms. Examples include cyclopropyl, cyclobutyl, cyclopentyl, cyclohexyl, methylcyclohexyl or adamantyl.

Examples for suitable substituted and unsubstituted aryl groups $R_2$ are: phenyl, 1-naphthyl and 2-naphthyl, each of which can be substituted by 1-3 halogen atoms, a phenyl group, 1-3 alkyl groups each of 1-4 carbon atoms, or a chloromethyl, fluoromethyl, trifluoromethyl, carboxy, $C_1$-$C_4$-alkoxy or hydroxy group. Substitution in the 3- and 4-positions on the phenyl ring is preferred, for example by fluorine, chlorine, $C_1$-$C_4$-alkoxy or trifluoromethyl, or in the 4-position by hydroxy.

Suitable heterocyclic groups $R_2$ include 5- and 6-membered heterocycles (e.g., aromatic) containing at least one hetero atom, (e.g., 1 or 2) preferably nitrogen, oxygen or sulfur. Examples include 2-furyl, 2-thienyl, 2-pyridyl, 4-pyridyl, 3-furyl, 3-thienyl, etc.

The alkylene group D can be straight-chain alkylene residues of 1-10 carbon atoms, or branched-chain, saturated and unsaturated alkylene residues of 1-10 or 2-10 carbon atoms, preferably of 1-5 or 2-5 carbon atoms, all of which can be optionally substituted by fluorine atoms. Examples include methylene, fluoromethylene, ethylene, 1,2-propylene, ethylethylene, trimethylene, tetramethylene, pentamethylene, 1-methyltetramethylene or 1-methyltrimethylene.

The alkyl groups $R_4$ and $R_5$ represent straight-chain or branched, saturated alkyl groups of 1–5 carbon atoms as already recited for $R_1$ and $R_2$. $R_5$ as halogen can be chlorine and bromine, preferably chlorine.

The functionally modified hydroxy groups in W and $R_3$ include acyloxy of 2–10 carbon atoms (e.g., alkanoyl) benzoyloxy, tetrahydropyranyloxy, tetrahydrofuranyloxy, trimethylsilyloxy, tribenzylsilyloxy, or dimethyl-tert-butylsilyloxy.

To prepare the clathrates of this invention, the compounds of general Formula I can be dissolved in a pharmacologically acceptable solvent, e.g., in an alcohol, preferably ethanol, in a ketone, e.g., acetone or in an ether, e.g. diethylether, and mixed with aqueous solutions of α-, β- or γ-cyclodextrin, preferably β-cyclodextrin, at 20° to 80° C.; or the acids of general Formula I in the form of the aqueous solutions of their salts (e.g., Na- or K-salts) can be admixed with a cyclodextrin and after solution with the equivalent amount of an acid (e.g., HCl or $H_2SO_4$) changed into the clathrates.

At this point or after cooling, the corresponding clathrates separate in the form of crystals. However, it is also possible to convert oily and also crystalline carbacyclins of Formula I by rather long stirring (e.g., for 1 hour to 14 days) at room temperature, by treatment with an aqueous solution of cyclodextrins, into the corresponding cyclodextrin crystalline form. The clathrates can be isolated as solid, free-flowing crystals by suctioning off and drying.

By selection of the suitable amounts of cyclodextrins and water it is possible to obtain the new clathrates in a stoichiometric composition with a reproducible content of effective substance. The clathrates can be used in a dry hygroscopic form or in a water-containing, but less hygroscopic form.

The starting material carbacyclins and α-, β- or γ-cyclodextrins, of course, are all known and/or readily preparable from known starting materials.

Suitable dextrins will include a wide variety of those which produce crystalline forms of carbacyclins as inclusion compounds. See, for example, J. E. F. Reynolds (ed.) Martindale, The Extra Pharmacopoeia 28th ed. The Pharmaceutical Press, London 1982, p. 333 and 389–390 and O.-A. Neumueller (ed.), Roempps Chemie-Lexikon, 8. Aufl. Franckh'sche Verlagshandlung, Stuttgart 1981, p. 763–764, 841, 1053–1054.

The clathrates produced in accordance with this invention are valuable pharmaceuticals.

Among the novel carbacyclin clathrates are those preferred compounds which have the following meaning of -A-W-D-E-$R_2$:

A-W-D-E-$R_2$ is —$C_{13}$≡≡≡$C_{14}$—CHOR—C$X_1$$X_2$—$CH_2$—$C_{18}$≡≡≡$C_{19}$—$CH_2X_3$

—$C_{13}$≡≡≡$C_{14}$— is —CH=CH— or —C≡C—

$X_1$ and $X_2$ independently are H, $CH_3$ or $C_2H_5$, and at least one of $X_1$ and $X_2$ is other than H, —$C_{18}$≡≡≡$C_{19}$— is $CX_4$=$CX_5$ or —C≡C— wherein $X_4$ and $X_5$ independently are H, $CH_3$ or $C_2H_5$ and $X_5$ can also be Cl, $X_3$ is H, $CH_3$ or $C_2H_5$.

The preferred stoichiometric ratio of Carbacyclin: -cyclodextrin (preferably) is 1:2 or 1:3.

For example, the clathrates of this invention have antihypertensive and brochodilatory activity. They are furthermore suitable for inhibiting thrombocyte aggregation. They show cytoprotective effects on the stomach, intestine, heart, on the liver, kidney, and on the pancreas. Consequently, the novel cyclodextrin clathrates of Formula I constitute valuable pharmaceutically active compounds. Moreover, they exhibit higher specificity and, above all, a substantially longer duration of activity, with a similar spectrum of effectiveness, compared with corresponding prostaglandins. Compared with $PGI_2$, they are distinguished by higher stability. The high tissue specificity of the novel prostaglandins is demonstrated in a study on smooth-muscle organs, such as, for example, on guinea pig ileum or isolated rabbit trachea, where a substantially lower stimulation can be observed than in the administration of natural prostaglandins of the E-, A-, or F-type.

The novel carbacyclin clathrates exhibit the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; treatment for stroke, prophylaxis and therapy of coronary heart disease, coronary thrombosis, cardiac infarction, peripheral arterial diseases, arteriosclerosis and thrombosis, prophylaxis and therapy of ischemic attacks on the CNS system, therapy for shock, inhibition of bronchoconstriction, inhibition of gastric acid secretion, cytoprotection of gastric and intestinal mucosa, cytoprotections in liver, kidney, heart, and in the pancreas, as well as in organ transplantations, antiallergic properties, lowering of pulmonary vascular resistance and of pulmonary blood pressure, promotion of renal blood flow, use in place of heparin or as an adjuvant in dialysis or hemofiltration, preservation of stored blood plasma, especially stored blood platelets, inhibition of labor, treatment of gestational toxicosis, enhancement of cerebral blood flow, etc. Furthermore, the novel carbacyclin clathrates exhibit antiproliferative and antidiarrheogenic properties.

The carbacyclin clathrates of this invention can also be employed in combination, for example, with β-blockers, diuretics, phosphodiesterase inhibitors, calcium antagonists, nonsteroidal anti-inflammatory agents, leukotriene synthesis inhibitors, leukotriene antagonists, thromboxane synthesis inhibitors, or thromboxane antagonists.

The clathrates of this invention can be utilized in liquid or solid galenic formulations wherein the formulations can be administered enterally, parenterally, vaginally, or rectally, or they can also be incorporated into surgical suture material or into synthetic resins.

For the production of tablets, the prostaglandincyclodextrin clathrate is mixed with excipients and auxiliary agents, such as lactose, cornstarch, polyvinylpyrrolidone and magnesium stearate.

For preparing solutions for enteral and parenteral use, the aqueous cyclodextrin clathrate solutions are lyophilized together with lactose. Subsequently, the lyophilized products can be brought to the desired concentration with physiological sodium chloride solution.

Consequently, the invention encompasses pharmaceutical preparations and formulations containing as the active ingredient a cyclodextrin clathrate of a carbacyclin analog.

Their use is entirely analogous to the known carbacyclins per se, e.g., iloprost. Thus, they can be administered in typical dosages of 1–1500 μg/kg/day (using unit dosages, e.g., of 0.01–100 mg) to treat the foregoing conditions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. Above and below, all temperatures are set forth uncorrected in degrees celsius; unless otherwise indicated, all parts and percentages are by weight.

EXAMPLE 1

At 80° C., 560 mg of β-cyclodextrin is dissolved in 4 ml of water; the solution is cooled to 60° C. and added dropwise to a warm solution of 60° C. of 18 mg of (5E)-(16RS)-16-methyl-18,18,19,19-tetradehydro-6a-carbaprostaglandin $I_2$ in 0.3 ml of ethanol. The mixture is agitated for 4 hours at 60° C., for one hour at 45° C., and for 16 hours at 25° C. The thus-precipitated solid matter is suctioned off, washed with 20 ml of a mixture of water/ethanol (1:1), and dried for 8 hours at 0.1 torr and 25° C. over phosphorus pentoxide, thus obtaining 340 mg of free-flowing crystals of the β-cyclodextrin clathrate of the above-mentioned carbacyclin analog.

The content of carbacyclin analog in the clathrate was determined by high-pressure liquid chromatography and amounted to 4.23%.

EXAMPLE 2

One gram of (5E)-(16S)-13,14-didehydro-16,20-dimethyl-3-oxa-18,18,19,19-tetradehydro-6a-carbaprostaglandin $I_2$ is stirred with 30.3 g of β-cyclodextrin in 214 ml of water for 48 hours at 25° C. The solid matter is suctioned off, washed with 15 ml of a mixture of water/ethanol (1:1), and dried for 24 hours at 0.1 torr and 25° C. over phosphorus pentoxide, thus obtaining 22.45 g of freely flowing crystals of β-cyclodextrin clathrate of the above-mentioned carbacyclin analog.

The content of carbacyclin analog in the clathrate was determined by titration and was 3.5%.

EXAMPLE 3

At 80° C., 41.75 g of β-cyclodextrin is dissolved in 298 ml of water, and a solution of 1.5 g of (5E)-(16S)-13,14-didehydro-1a,1b-dihomo-16,20-dimethyl-3-oxa-18,18,19,19-tetradehydro-6a-carbaprostaglandin $I_2$ in 24 ml of ethanol is added dropwise within 15 minutes. The mixture is stirred for 4 hours at 60° C. and then is allowed to cool off overnight under agitation. The thus-precipitated solid matter is suctioned off, washed with 50 ml of a mixture of water/ethanol (1:1), and dried for 24 hours at 0.1 torr and 25° C. over phosphorus pentoxide, thus obtaining 38 g of free-flowing crystals of the β-cyclodextrin clathrate of the aforementioned carbacyclin analog.

The content of carbacyclin analog in the clathrate was determined by titration and amounted to 3.3%.

EXAMPLE 4

At 25° C., 0.5 g of (5E)-(16S)-13,14-didehydro-16,20-dimethyl-18,18,19,19-tetradehydro-6a-carbaprostaglandin $I_2$ is stirred with 15 g of β-cyclodextrin in 110 ml of water for 50 hours. The solid matter is suctioned off, washed with about 10 ml of a mixture of water-ethanol (1:1), and dried for 24 hours at 0.1 torr and 25° C. over phosphorus pentoxide, thus obtaining 11 g of free-flowing crystals of the β-cyclodextrin clathrate of the above-mentioned carbacyclin analog.

The content of carbacyclin analog in the clathrate was determined by titration and was 3.6%.

EXAMPLE 5

At 45° C., 57.75 g of β-Cyclodextrin is dissolved in 1.53 l of water; a solution of 7.633 g of (5E)-(16 RS)-16-methyl-18,18,19,19-tetradehydro-6a-carbaprostaglandin $I_2$ in 45 ml of ethanol is added dropwise under agitation within 30 minutes. After cooling to 25° C., within 1 hour the mixture is stirred for 2 hours at this temperature and 3 hours at 0° C. The solid matter is suctioned off, washed with ice-cold water, acetone and with water again.

(a) After drying in vacuo and storage at normal conditions until the weight is constant, 56.01 g (93.9%) of free-flowing crystals of the β-cyclodextrin clathrate of the aforementioned carbacyclin analog containing 6% of water and 12.8% of the active ingredient (determined by titration) are obtained.

(b) After drying over $P_2O_5$ (vacuo) 52.7 g of free-flowing hygroscopic crystals containing 13.6% of the active ingredient (determined by titration) are obtained.

EXAMPLE 6

After saponification of 3.877 g (5E)-(16 S)-13,14-Didehydro-16,20-dimethyl-3-oxa-18,18,19,19-tetradehydro-6a-carba-prostaglandin-$I_2$-tert.-butylester with 11.7 ml of 1N NaOH, ether-extraction of impurities and dilution with water to 660 ml, 24.52 g of β-Cyclodextrin are added. The mixture is warmed to 26° C. under agitation until solution. After adding of 11.7 ml of 1N HCl within 30 minutes and stirring for 90 minutes, the solution was warmed to 55° C. After cooling to 25° C. within 1 hour, stirring an additional hour at this temperature and 2.5 hours at 0° C., the solid material is suctioned off, washed with ice-cold water and dried as described in example 5.

(a) 22.53 g (89.2%) of free-flowing crystals containing 7.2% of water and 13.36% of active compound are obtained.

(b) 21.0 g of free-flowing hygroscopic crystals containing 14.3% of the active ingredient are obtained.

EXAMPLE 7

At 50° C. a solution of 1.456 g (5 E)-(16 S)-13,14-Didehydro-1a,1b-dihomo-16,20-dimethyl-18,18,19,19-tetradehydro-6a-carbaprostaglandin-$I_2$ in 6 ml ethanol are dropped within 30 minutes into a solution of 14.30 g of β-Cyclodextrin in 205 ml of water.

After cooling to 20° C. within 1 hour, stirring for 2 hours at this temperature and 18 hours at 0° C., the solid material is suctioned off, washed with ice-cold water and dried as in example 5.

(a) 14.155 g (95.8%) of free-flowing crystals containing 7.6% of water and 9.9% of the active ingredient are obtained.

(b) 13.1 g of free-flowing hygroscopic crystals containing 10.7% of active ingredient are obtained.

EXAMPLE 8

(5E)-(16S)-13,14,18,18,19,19-hexadehydro-16,20-dimethyl-6a-carba-prostaglandin-I$_2$-β-cyclodextrin clathrate.

By reaction of (5E)-(16S)-13,14,18,18,19,19-hexadehydro-16,20-dimethyl-6a-carba-prostaglandin I$_2$ and β-cyclodextrinclathrate corresponding to example 1, the title compound is formed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition, comprising a cyclodextrin clathrate of a carbacyclin of the formula $$\text{(I)}$$

wherein
R$_1$ is hydrogen, alkyl of 1-10 carbon atoms, alkenyl of 2-10 C-atoms, or C$_{1-10}$ alkyl or C$_{2-10}$ alkenyl substituted by C$_{6-10}$-aryl or C$_{6-10}$ aryl substituted as defined for R$_2$ below,
A is —CH$_2$CH$_2$—, trans-CH=CH—, or —C≡C-group,
W is —CHOR— or $$\begin{array}{c} CH_3 \\ | \\ C- \\ | \\ OR \end{array}$$

wherein
the OR-group can be in the α- or β-position,
D is C$_{1-10}$-alkylene, C$_{2-10}$-alkenylene, or C$_{1-10}$-alkylene or C$_{2-10}$-alkenylene each substituted by fluorine
m is 1, 2 or 3,
E is —C≡C—, or —CR$_4$=CR$_5$—,
R$_4$ is hydrogen or alkyl of 1-5 carbon atoms,
R$_5$ is hydrogen, halogen, or alkyl of 1-5 carbon atoms,
R$_2$ is alkyl of 1-10 carbon atoms, alkenyl of 2-10 C-atoms, C$_{1-10}$ alkyl or C$_{2-10}$ alkenyl substituted by C$_{6-10}$-aryl or C$_{6-10}$ aryl substituted as defined for R$_2$ below, cycloalkyl of 3-10 carbon atoms, C$_{3-10}$-cycloalkyl substituted by C$_{1-4}$-alkyl, aryl of 6-10 carbon atoms, C$_{6-10}$-aryl substituted by 1-3 halogen atoms, a phenyl group, 1-3 alkyl groups each of 1-4 carbon atoms, or a chloromethyl, fluoromethyl, trifluoromethyl, carboxy, C$_1$-C$_4$-alkoxy or hydroxy group or an aromatic heterocycle of 5- or 6-members containing 1 or 2 O, S, or N hetero atoms,
R$_3$ is OR,
n is 1, 2, 3, 4 or 5,
X is —CH$_2$ or an oxygen atom, and
R is H or C$_{1-10}$-acyl derived from a hydrocarbon aliphatic carboxylic acid, or is benzoyloxy, tetrahydropyranyloxy, tetrahydrofuranyloxy, trimethylsilyloxy, tribenzylsilyloxy, or dimethyl-tertbutylsilyloxy
and a pharmaceutically acceptable excipient.

2. A pharmaceutical composition of claim 1, wherein the clathrate is (5E)-(16RS)-16-methyl-18,18,19,19-tetradehydro-6a-carbaprostaglandin I$_2$ β-cyclodextrin clathrate.

3. A pharmaceutical composition of claim 1, wherein the clathrate is (5E)-(16S)-13,14-didehydro-16,20-dimethyl-3-oxa-18,18,19,19-tetradehydro-6a-carbaprostaglandin I$_2$ β-cyclodextrin clathrate.

4. A pharmaceutical composition of claim 1, wherein the clathrate is (5E)-(16S)-13,14-didehydro-1a,1b-dihomo-16,20-dimethyl-3-oxa-18,18,19,19-tetradehydro-6a-carbaprostaglandin I$_2$ β-cyclodextrin clathrate.

5. A composition of claim 1 wherein in said carbacyclin R$_1$ and R$_2$ are alkyl of 1-7 carbon atoms.

6. A composition of claim 1 wherein said cycloalkyl is cyclopropyl, cyclobutyl, cyclopentyl, cyclohexyl, methylcyclohexyl or adamantyl.

7. A composition of claim 1 wherein said R$_2$ is phenyl or 1- or 2-naphthyl.

8. A composition of claim 1 wherein R$_2$ is 2-furyl, 2-thienyl, 2-pyridyl, 4-pyridyl, 3-furyl or 3-thienyl.

9. A composition of claim 1, wherein D is methylene, fluoromethylene, ethylene, 1,2-propylene, ethylethylene, trimethylene, tetramethylene, pentamethylene, 1-methyltetramethylene or 1-methyltrimethylene.

10. A composition of claim 1 wherein R$_4$ and R$_5$ are alkyl.

11. A composition of claim 1 wherein R is H.

12. A composition of claim 1 wherein said cyclodextrin is α-, β- or γ-cyclodextrin.

13. A composition of claim 1 wherein said cyclodextrin is β-cyclodextrin.

14. A cyclodextrin clathrate of a carbacyclin of the formula wherein $R_1$ is hydrogen, alkyl of 1–10 carbon atoms, alkenyl of 2–10 C-atoms, or $C_{1-10}$ alkyl or $C_{2-10}$ alkenyl substituted by $C_{6-10}$-aryl or $C_{6-10}$ aryl substituted as defined for $R_2$ below, A is a —$CH_2CH_2$—, trans-CH=CH—, or —C≡C- group, W is —CHOR— or

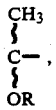

wherein the OR-group can be in the $\alpha$- or $\beta$-position,

D is $C_{1-10}$-alkylene, $C_{2-10}$-alkenylene, or $C_{1-10}$-alkylene or $C_{2-10}$-alkenylene each substituted by fluorine m is 1, 2 or 3, E is —C≡C—, or —$CR_4$=$CR_5$—, $R_4$ is hydrogen or alkyl of 1–5 carbon atoms, $R_5$ is hydrogen, halogen, or alkyl of 1–5 carbon atoms, $R_2$ is alkyl of 1–10 carbon atoms, alkenyl of 2–10 C-atoms, $C_{1-10}$ alkyl or $C_{2-10}$ alkenyl substituted by $C_{6-10}$-aryl or $C_{6-10}$ aryl substituted as defined for $R_2$ below, cycloalkyl of 3–10 carbon atoms, $C_{3-10}$-cycloalkyl substituted by $C_{1-4}$-alkyl, aryl of 6–10 carbon atoms, $C_{6-10}$-aryl substituted by 1–3 halogen atoms, a phenyl group, 1–3 alkyl groups each of 1–4 carbon atoms, or a chloromethyl, fluoromethyl, trifluoromethyl, carboxy, $C_1$-$C_4$-alkoxy or hydroxy group, or an aromatic heterocycle of 5- or 6-members containing 1 or 2 O, S, or N hetero atoms, $R_3$ is OR, n is 1, 2, 3, 4 or 5, X is —$CH_2$ or an oxygen atom, and R is H or $C_{1-10}$-acyl derived from a hydrocarbon aliphatic carboxylic acid, or is benzoyloxy, tetrahydropyranyloxy, tetrahydrofuranyloxy, trimethylsilyloxy, tribenzylsilyloxy, or dimethyl-tertbutylsilyloxy.

15. A compound of claim 14 wherein the cyclodextrin is $\alpha$-, $\beta$- or $\gamma$-cyclodextrin.

16. A compound of claim 14 wherein the cyclodextrin si $\beta$-cyclodextrin.

17. A cyclodextrin clathrate of claim 14 wherein A-W-D-E-$R_2$ is —$C_{13}$≡≡≡$C_{14}$—CHOR—$CX_1X_2$—$CH_2$—$C_{18}$≡≡≡$C_{19}$—$CH_2X_3$ —$C_{13}$≡≡≡$C_{14}$ is —CH=CH— or —C≡C—

$X_1$ and $X_2$ independently are H, $CH_3$ or $C_2H_5$, and at least one of $X_1$ and $X_2$ is other than H, —$C_{18}$≡≡≡$C_{19}$— is $CX_4$=$CX_5$ or —C≡C— wherein $X_4$ and $X_5$ independently are H, $CH_3$ or $C_2H_5$ and $X_5$ can also be Cl, $X_3$ is H, $CH_3$ or $C_2H_5$.

18. A composition of claim 1 wherein in the clathrate, A-W-D-E-$R_2$ is —$C_{13}$≡≡≡$C_{14}$—CHOR—$CX_1X_2$—$CH_2$—$C_{18}$≡≡≡$C_{19}$—$CH_2X_3$ —$C_{13}$≡≡≡$C_4$ is —CH=CH— or —C≡C—

$X_1$ and $X_2$ independently are H, $CH_3$ or $C_2H_5$, and at least one of $X_1$ and $X_2$ is other than H, —$C_{18}$≡≡≡$C_{19}$— is $CX_4$=$CX_5$ or —C≡C— wherein $X_4$ and $X_5$ independently are H, $CH_3$ or $C_2H_5$ and $X_5$ can also be Cl, $X_3$ is H, $CH_3$ or $C_2H_5$.

19. A method of treating cardiac infarction or a peripheral arterial disease by administering an effective amount of a carbacyclin comprising administering the carbacyclin in the form of a cyclodextrin clathrate of claim 14.

20. A method of treating cardiac infarction or a peripheral arterial disease by administering an effective amount of a carbacyclin comprising administering the carbacyclin in the form of a cyclodextrin clathrate of claim 17.

21. A method of claim 19, wherein the administration is oral.

22. A method of claim 20, wherein the administration is oral.

* * * * *